United States Patent [19]
Fedorov et al.

[11] Patent Number: 5,392,079
[45] Date of Patent: * Feb. 21, 1995

[54] KERATOMETER

[76] Inventors: Svyatoslav N. Fedorov, pereulok Dostoevskogo,1/21,kv.32; Daniil T. Puryaev, ulitsa Srednvava Pervomaiskava,27,kv.36; Alexandr V. Laskin, Izmailovsky prospekt,73/2,kv.58, all of Moscow, U.S.S.R.

[*] Notice: The portion of the term of this patent subsequent to Aug. 21, 2010 has been disclaimed.

[21] Appl. No.: 567,826

[22] Filed: Aug. 15, 1990

[51] Int. Cl.$^6$ ................................. A61B 3/10
[52] U.S. Cl. ..................................... 351/212
[58] Field of Search ............... 351/212, 211, 221, 219

[56] References Cited
U.S. PATENT DOCUMENTS

| | | | |
|---|---|---|---|
| 3,639,043 | 2/1972 | Townsley | 351/212 |
| 4,772,115 | 9/1988 | Gersten et al. | 351/212 |
| 4,964,715 | 10/1990 | Richards | 351/212 |

Primary Examiner—Paul M. Dzierzynski

[57] ABSTRACT

The keratometer comprises an illumination system made as the following components located before a cornea: a light source, an objective lens, ring-shaped measuring marks interposed between the light source and the objective lens on the focal surface of the illumination system symmetrically with respect to the optic axis of the objective lens, and a cone-shaped mirror.

The cone-shaped mirror is interposed between the objective lens of the illumination system and the cornea and is shaped as a cone frustum having its inner surface provided with a reflecting coating. The keratometer comprises also a unit for recording the images of the measuring marks and a projection lens, the latter being composed of two elements one of which is in fact the objective lens of the illumination system and the other element is located on the optic axis of the illumination system objective lens between the latter and the unit for recording the images of the measuring marks.

3 Claims, 2 Drawing Sheets

KERATOMETER

FIELD OF THE INVENTION

This invention relates to ophthalmological apparatus for determining the topography of the corneal surface and has particular reference to a keratometer.

The invention can find most utility when applied for selection of contact lenses and for control of the corneal shape on ophthalmic microsurgery.

The invention is also applicable for control of the shape of aspheric surfaces of some optical components, such as lenses and mirrors.

At present there is encountered the problem of accurate determination of the topography of a patient's corneal surface, said problem stemming from introduction of novel methods of sight correction into medical practice, such as use of contact lenses and microsurgery on the cornea. Knowledge of the corneal topography is indispensable for making contact lenses the geometric parameters of the posterior surfaces of which must follow the corneal surface of the eye being corrected, as well as for control of the shape of the corneal surface during microsurgical procedures.

Known in the present state of the art are diverse methods for determining the corneal surface, including such as taking casts of the eye, ultrasonic location, taking photos of the profile of the corneal surface, photoslit sections, stereophotogrammetry, moiré topomerry, interferometry, etc. However, all the methods mentioned above suffer from disadvantages that prevent their extensive application in ophthalmological practice. It is keratometry that proves to be an optimum method of determining the geometric parameters of the corneal surface, which is capable of obtaining an encoded topogram of the corneal surface, i.e., a keratogram with the aid of a special instrument, that is, a keratometer. Thus, the coordinate of points on the corneal surface is determined by decoding the keratogram obtained.

BACKGROUND OF THE INVENTION

One state-of-the-art keratometer for determining the topography of the corneal surface (SU, A, 1,115,716) is known to comprise a source of light, measuring marks shaped as concentric reflecting rings and a radial grid, which are located on a spherical concave surface whose axis is aligned with the optic axis of a projection lens, wherein use is made of a telecentric path of light rays in the object space.

A cardinal disadvantage of the known keratometer resides in that the measuring marks are situated at a final distance from the corneal surface, which provides for but a little area of the cornea arrangement zone within which cornea displacement will not affect adversely the measurement accuracy. Besides, such a little area of the cornea arrangement prevents pinpoint-accuracy measurement of the surface of corneas featuring high degree of asphericity. Another disadvantage inherent in the construction in question is the use of large-diameter (over 150 mm) concentric rings as the measuring marks, since high-accuracy production of such rings comes across some technological difficulties, whereas production inaccuracies of the rings affect adversely the measurement accuracy.

Further disadvantages of the known keratometer reside in its large overall dimensions and mass. On the other hand, the necessity for accurate orientation of the corneal surface with respect to the instrument and accurate setting of the measuring marks involves further complication of the keratometer construction. In addition, a patient's head is located close to the instrument during the measuring procedure, thus presenting inconvenience to the patient. The disadvantages mentioned above make impossible an efficient use of the keratometer in the practice of medical studies and rules out completely a possibility of its application in carrying out microsurgical procedures on the eye.

One more keratometer (SU, A, 1,337,042) is known to comprise an illumination system which incorporates the following components located before the cornea: a light source, an objective lens in the form of a spherical lens, measuring marks interposed between the light source and the spherical lens and made as luminous holes in a diaphragm shaped as a concave sphere whose centre is aligned with the centre of the spherical lens, the principal sections of prisms with two reflecting faces being situated in the meridional planes of said spherical lens. The aforesaid prisms are so oriented that the beams of parallel light rays emerging from the spherical lens at different angles and reflected from said prisms, intersect in the zone of location of the cornea under examination, and the projection lens makes use of a telecentric path of light rays in the object space.

A substantial disadvantage from which the known keratometer suffers resides in discreteness of the measuring marks, which fails to provide a required accuracy of measurement of the surface of unsymmetrically shaped corneas, since the shape of an entire corneal surface is judged by the results of measurement of its separate portions. Besides, manufacture of a spherical lens and a great many prisms offers some technological difficulties, while installation of such prisms involves further sophistication of the construction of the keratometer in question, as well as increasing of its overall dimensions and mass. Moreover, the keratometer construction fails to provide convenience in carrying out medical studies since it requires that a patient's head be situated close to the instrument, which is inconvenient for the patient.

OBJECTS AND SUMMARY OF THE INVENTION

It is an object of the present invention to provide higher accuracy of measuring the topography of the corneal surface.

It is another object of the present invention to provide higher rate of measurements.

It is one more object of the present invention to provide substantially reduced overall dimensions and mass of the instrument.

Said object is accomplished due to the fact that in a keratometer, comprising an illumination system, which consists of the following components located before the cornea: a light source, an objective lens, measuring marks interposed between the light source and the objective lens and arranged symmetrically with respect to the optic axis of the latter, a projection lens, and a unit for recording the images of the measuring marks, according to the invention, the illumination system comprises a conical mirror interposed between the objective lens of the illumination system and the cornea and shaped as a cone frustum having a reflecting coating on its inner surface, the cone axis being aligned with the optic axis of the objective lens of the illumination system and with that of the projection lens, while the measuring marks are ring-shaped and are located on the focal surface of the illumination system and the projection lens is composed of at least two components one of which is essentially the objective lens of the illumination system, while the other is situated on the optic axis of the objective lens of the illumination system between said lens and the unit for recording the images of the measuring marks.

The proposed keratometer is capable of providing higher accuracy of measurement of the corneal surface topography, while application of a conical mirror makes it possible to use half the number of measuring marks for the same amount of the topographic angles as in the heretofore-known keratometers and use of greater-diameter marks (in excess of 150 mm) which can be manufactured at a lower accuracy than smaller-diameter marks, is dispensed with.

The proposed invention is instrumental in attaining higher accuracy of measurement of the topography of the surface of highly aspherical corneas, which is attained due to an extended zone of the cornea location and by using a projection lens featuring a small back aperture, which adds to the depth of definition as compared with the heretofore-known keratometers. Extension of the zone of location of the cornea is attained due to collimation of the light beams running from the measuring marks and incident upon the cornea, for which purpose the measuring marks are situated on the focal surface of the illumination system, as well as due to the fact that the projection lens makes use of a telecentric path of light rays in the object space, in view of which the aperture diaphragm is disposed in the back focal plane of the projection lens. The images of the measuring marks in the proposed keratometer appear as closed rings, therefore the number of the meridional sections, wherein the corneal shape is studied is practically unlimited, whereby the accuracy of measurement of the surfaces of unsymmetrically shaped corneas is increased.

The proposed keratometer enables the rate of measurement to be increased, which is attained due to an extended zone of the cornea location, since such an extension of the zone makes it possible to considerably cut down the preoperative instrument adjustment time.

Use of at least one convergent lens as the objective lens of the illumination system enables one to simplify the keratometer construction, since the amount of its components is reduced.

Arrangement of the conical mirror in such a manner that the greater base of a cone frustum faces the objective lens of the illumination system makes it possible to reduce the overall dimensions and mass of the instrument and to simplify its construction due to reduced maximum diameter of the measuring marks, which first and foremost determine the overall dimensions of the instrument as a whole, as well as due to a decreased amount of construction elements of the instrument.

BRIEF DESCRIPTION OF THE DRAWINGS

The essence of the invention will become more evident from the following detailed description of its specific exemplary embodiment to be read with reference to the accompanying drawings, wherein.

Figure 1:
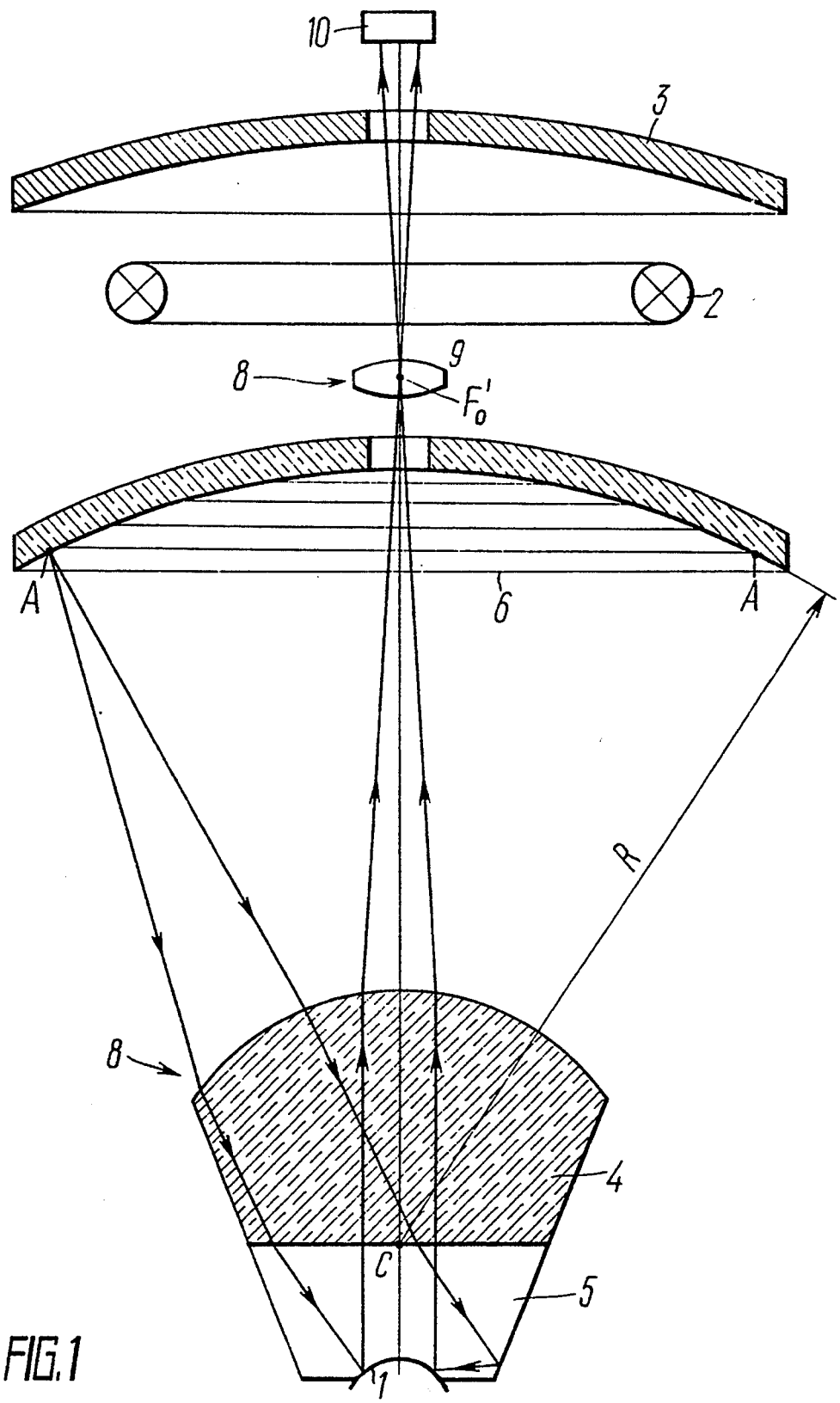
FIG. 1 is a general diagrammatic view of a keratometer, according to the invention.

The keratometer of the present invention comprises an illumination system, which consists of the following components placed before a cornea 1 (FIG. 1): a light source 2 with a reflector 3, an objective lens 4, which is in fact a plano-convex convergent lens, a conical mirror 5 interposed between the plano-convex lens 4 and the cornea 1. Interposed between the light source 2 and the plano-convex lens 4 are ring-shaped measuring marks 6 disposed symmetrically with respect to the optic axis of the lens 4 on a concave spherical surface, having a radius $R$, of a meniscus lens 7. The keratometer comprises also a projection lens 8 composed on two elements, i.e., the plano-convex lens 4 and an objective lens 9, the centre of whose entrance pupil is aligned with the back focal point $F'_o$ of the plano-convex lens 4, and a unit 10 for recording the images of the measuring marks 6. The point C is in effect the centre of the convex spherical surface of the lens 4. The conical mirror 5 is shaped as a hollow cone frustum whose greater base is integrated with the plane surface of the lens 4, while the cone vertex (the point K in FIG. 2) faces the cornea 1 under examination. The inner surface of the cone has a reflecting coating and its axis is aligned with the optic axis of the lens 4. The thickness of the lens 4 equals the radius of its convex spherical surface, therefore the centre C of the spherical surface of the lens 4 is located on its plane surface. The measuring marks 6 are in fact ring-shaped light-dispersing lines. The concave spherical surface of the meniscus lens 7 is arranged concentrically with the convex spherical surface of the lens 4 close to its back focal sphere, which provides for collimation of the beam of light rays running from the measuring marks 6. The latter can be made by, e.g., engraving the rings of a required diameter on the concave spherical surface, which has previously keen coated with a reflecting layer, whereupon a layer of an opaque material such as lacquer has been deposited. That is why when the lens 7 is illuminated by the light source 2 only these light rays are incident upon the cornea 1 being examined, which run from the measuring marks 6.

Figure 2:
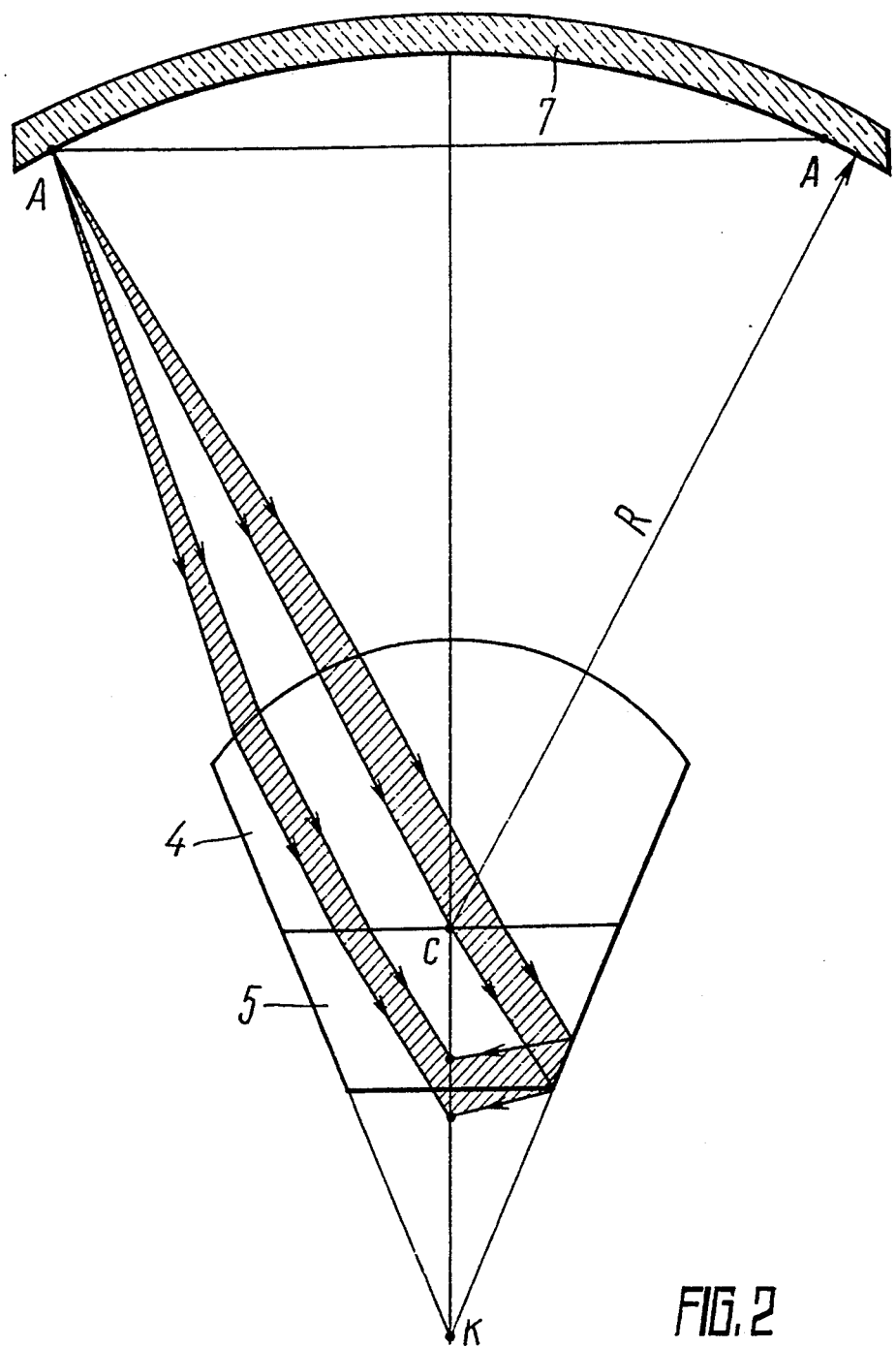
FIG. 2 is an illumination diagram of the cornea location zone.

The keratometer functions as follows (FIG. 1). The patient is so positioned that the cornea 1 under examination be on the axis of the keratometer. Light rays emerging from the light source 2 and reflected from the reflector 3 illuminate the measuring marks 6. Since the latter are located nearby the focal sphere of the lens 4 so the light rays having been refracted on its surface emerge from the lens 4 as parallel beams. A broad inclined parallel beam of rays leaving the plane surface of the lens 4, is partly reflected from the conical surface of the mirror 5 and partly gets incident on the surface of the cornea 1, which is indicated by a path diagram of lights running from the points A of the measuring mark 6 (FIGS. 1, 2) that are most removed from the axis. It is due to the aforesaid fact that the beams of parallel light rays pass to the zone of location of the cornea 1 being examined, the angle of inclination of said rays to the axis being known accurately, since the construction parameters of the keratometer principal scheme is a matter of knowledge. Among the light rays reflected from the cornea there occur always such that run parallel to the optic axis until meeting the convex spherical surface of the lens 4, while past the latter lens said rays are focused at the focal point $F'_o$ coincident with the centre of entrance pupil of the objective lens 9 (FIG. 1). The light rays reflected from the surface of the cornea 1 define the images of the measuring marks 6 as diverging beams of rays incident on the objective lens 9, the principal rays of said beams passing parallel to the optic axis in the space between the cornea 1 being examined and the convex surface of the lens 4. Thus, a telecentric path of light rays in the object space is made use of in the instrument. The unit 10 shapes the images of the measuring marks 6 as constructed by different portions of the surface of the cornea 1. Then the topography of the surface of the cornea 1 is found by measuring the coordinates of these images and by proceeding from the knowledge of the angles of inclination of the beams of parallel light rays illuminating the cornea 1 to the optic axis. The keratometer is positioned with respect to the cornea 1 under examination using conventional techniques.

What is claimed is:

1. A keratometer, comprising: an illumination system made as the following components located before the cornea: a light source, an objective lens, ring-shaped measuring marks interposed between said light source and said objective lens on the focal surface of said illumination system and arranged symmetrically with respect to the optic axis of said objective lens, a conical mirror interposed between said objective lens and said cornea, said conical mirror being shaped as a cone frustum having a reflecting coating on its inner surface, the axis of said cone frustum being aligned with said optic axis of the objective lens; a projection lens; a unit for recording the images of said measuring marks; said projection lens is composed of at least two components of which one is in fact said objective lens of said illumination system, while the other component is located on said optic axis of said objective lens of the illumination system between said objective lens and said unit for recording the images of the measuring marks.

2. A keratometer as claimed in claim 1, wherein said objective lens of the illumination system comprises at least one convergent lens.

3. A keratometer as claimed in claim 1, wherein the greater base of said conical mirror faces said objective lens of the illumination system.

* * * * *